United States Patent [19]

Riedl

[11] 4,060,542
[45] Nov. 29, 1977

[54] 14-DESOXY-14 THIOCYANATO-ACETOXY-MUTILIN

[75] Inventor: Kurt Riedl, Kufstein, Austria

[73] Assignee: Biochemie Gesellschaft m.b.H., Vienna, Austria

[21] Appl. No.: 700,114

[22] Filed: June 28, 1976

Related U.S. Application Data

[60] Division of Ser. No. 416,246, Nov. 15, 1973, Pat. No. 3,979,423, which is a continuation of Ser. No. 261,335, June 9, 1972, abandoned, which is a continuation-in-part of Ser. No. 57,761, June 23, 1970, abandoned.

[30] Foreign Application Priority Data

July 25, 1969 Austria .................................. 7223/69

[51] Int. Cl.² ................. C07C 161/02; C07C 161/04

[52] U.S. Cl. .......................... 260/454; 260/326.12 R; 260/141; 260/349; 260/455 B; 260/456 P; 260/482 R; 260/484 R; 260/484 A; 260/484 P; 260/485 R; 560/147; 260/487; 560/155; 560/190; 560/226; 560/231; 426/2; 426/532; 424/226; 424/311; 424/313

[58] Field of Search ........................................ 260/454

[56] References Cited

PUBLICATIONS

Birch et al., Tetrahedron, vol. of 1966, supplement 8, part I, pp. 359–387.
Sneed et al., "Comprehensive Inorganic Chemistry", vol. 3, pp. 223–225 (1954).
Thorne et al., "Fritz Ephraim's Inorganic Chemistry", p. 242 (1948).

Primary Examiner—Floyd D. Higel
Attorney, Agent, or Firm—Browdy and Neimark

[57] ABSTRACT

A pleuromutilin derivative which is 14-desoxy-14-thiocyanatoacetoxy-mutilin is useful as an animal feed additive to increase meat production and also finds application in veterinary medicine as an antibiotic.

1 Claim, No Drawings

14-DESOXY-14 THIOCYANATO-ACETOXY-MUTILIN

This application is a division of application Ser. No. 416,246, filed Nov. 15, 1973, now U.S. Pat. No. 3,979,423, itself a continuation of application Ser. No. 261,335, filed June 9, 1972, now abandoned, Ser. No. 261,335 in turn being a continuation-in-part of application Ser. No. 57,761, filed June 23, 1970, now abandoned.

The present invention relates to new pleuromutilin derivatives of formula I,

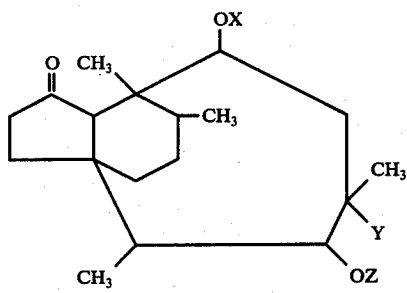

wherein X, Y and Z are as defined in any one of the following groups:

i. X is -CO-CH$_2$-R$_1$ wherein R$_1$ is chlorine, bromine, iodine, thiocyanato, azido, dithiocarbonic acid-O-alkyl (C$_1$ to C$_5$), (N,N-tetramethylene-thiocarbamoyl)-mercapto, -S-phenyl, -S-phenyl substituted by carboxyl or by one or two hydroxyl radicals, -S-pyridyl, -S-alkyl(C$_1$ to C$_5$), or -S-alkyl(C$_1$ to C$_5$) substituted by one or more amino hydroxyl or carboxyl radicals, Y is vinyl, and Z is hydrogen, ii. X is -CO-CO-OH, Y is vinyl, and Z is hydrogen, iii. X is -CO-CH$_2$-NH$_2$, Y is ethyl, and Z is hydrogen,, iv. 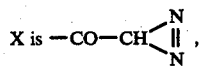

Y is ethyl, and Z is hydrogen, v. X is hydrogen, Y is vinyl, and Z is acetyl, or vi. X is —COR$_2$, wherein R$_2$ is alkyl of 1 to 5 carbon atoms, Y is vinyl, and Z is hydrogen.

a. a compound of formula Ia,

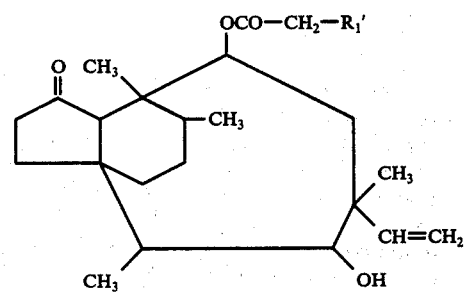

wherein R$_1$' includes all the significances of R$_1$ as defined above, other than amino, is obtained by reacting 14-desoxy-14-tosyloxyacetoxymutilin of formula II

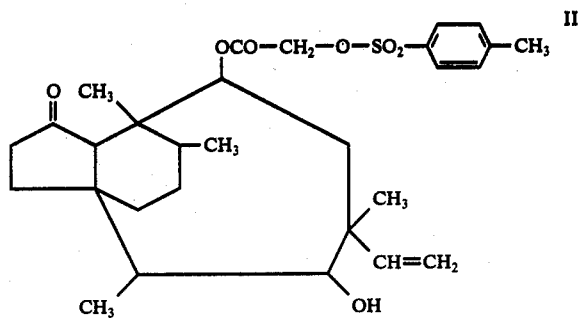

with a compound of formula III,

Me—R$_1$    III wherein R$_1$ is as defined above, and
Me is an alkali metal, b. the compound of formula Ib

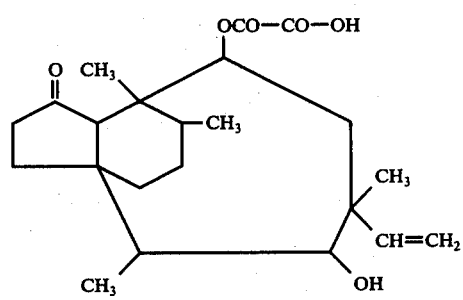

is obtained by oxidizing pleuromutilin of formula IV,

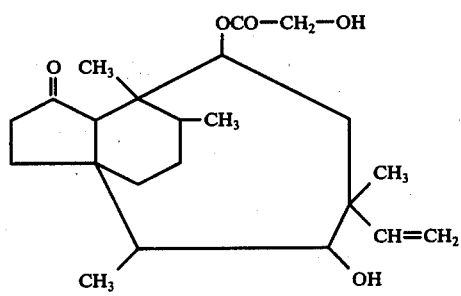

c. the compound of formula Ic

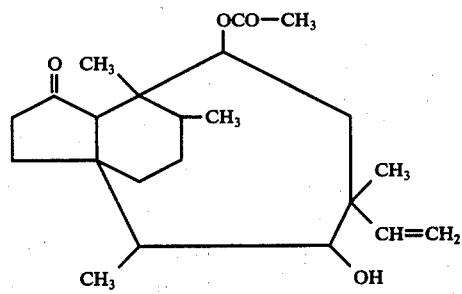

is obtained by reducing a compound of formula Id,

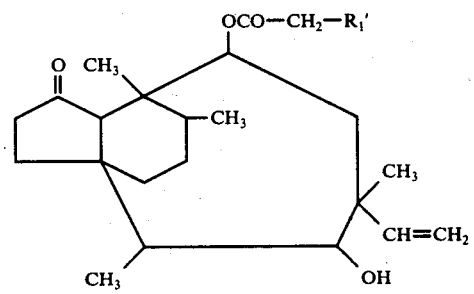

wherein R$_1'$ is bromine, iodine or thiocyanato, d. the compound of formula Ie

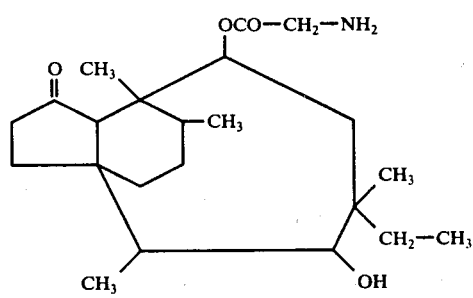

is obtained by hydrogenating the compound of formula If,

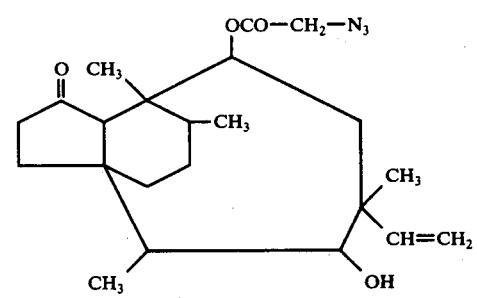

e. the compound of formula Ig

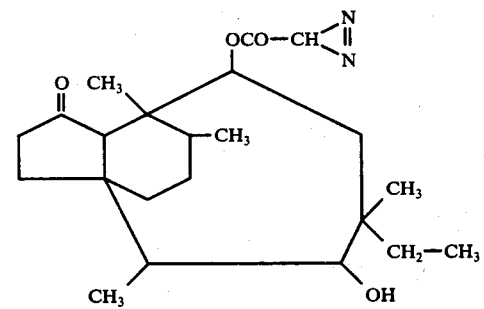

is obtained by diazotizing the compound of formula Ie f. the compound of formula Ih

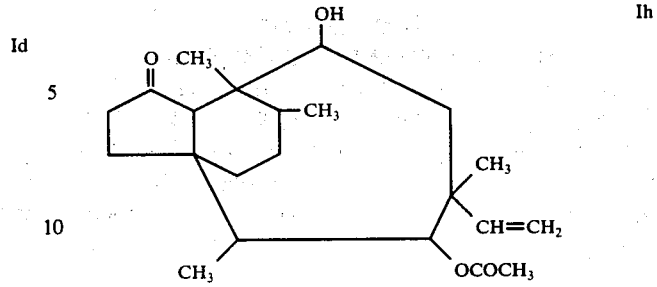

is obtained by selective saponification of a compound of formula V,

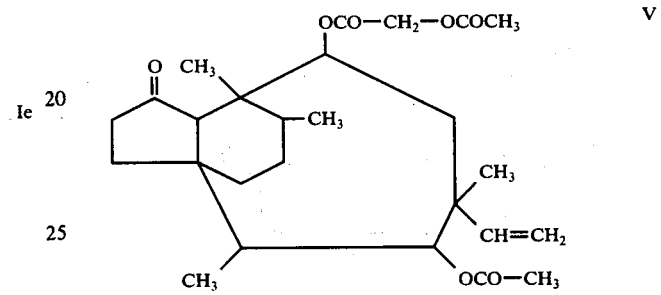

or (g) a compound of formula Ii,

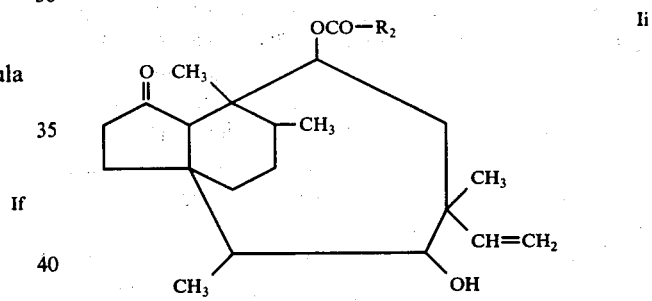

wherein R$_2$ is alkyl of 1 to 5 carbon atoms, is obtained by selective saponification of a compound of formula VI,

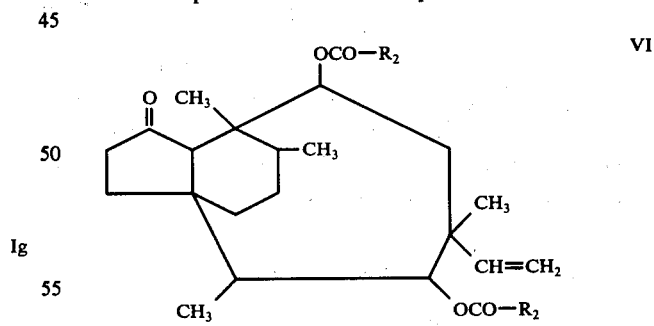

wherein R$_2$ is as defined above,

Process (a) may be effected either in a water-miscible inert organic solvent, e.g. acetone, methylethyl ketone, ethanol, methanol or dimethyl formamide, optionally in the presence of water, or in a water-immiscible inert organic solvent. A suitable reaction temperature ranges between 20° and 60° C, preferably 20° and 50° C. When the reaction is effected in acetone, a precipitate of alkali tosylate results, this being optionally filtered off.

Oxidation of pleuromutilin of formula IV in accordance with process (b) may, for example, be effected with activated manganese dioxide in the presence of a basic agent such as potassium or sodium carbonate, and in acetone as solvent. The reaction is conveniently effected at the boiling temperature of the reaction mixture for a period of approximately 4 to 5 hours.

Reduction of compounds of formula Id in accordance with process (c) is preferably effected with coarse aluminium amalgam powder in an inert organic solvent, e.g. absolute ethanol or isopropanol, at the boiling temperature of the reaction mixture. A reaction period of 2 to 4 hours is sufficient.

Hydrogenation of the compound of formula If in accordance with process (d) is conveniently effected with hydrogen in the presence of a hydrogenation catalyst such as palladium on charcoal, in a suitable solvent, e.g. glacial acetic acid, the reaction being effected at room temperature.

Diazotization of the compound of formula Ie in accordance with process (e) is conveniently effected in an aqueous acid solution, e.g. dilute hydrochloric acid, by the addition of sodium nitrite. In this case the reaction temperature should preferably be maintained at −10° to +5° C by external cooling.

Selective saponification of the compound of formula V in accordance with process (f) is conveniently effected in an acid medium, preferably a mixture of a mineral acid and a water-miscible inert organic solvent such as dilute hydrochloric acid in acetone. Saponification is effected at a temperature ranging between 40° and 90° C, preferably 50° and 70° C, for a period of 30 to 60 minutes.

Selective saponification of compounds of formula VI in accordance with process (g) is conveniently effected in an alkaline medium, preferably a solution of a strong inorganic base such as sodium hydroxide, in a lower alcohol such as ethanol. Saponification is effected at a temperature ranging between 20° C and the boiling temperature of the mixture, preferably at the boiling temperature, for a period of 1 to 4 hours.

The compounds of formula I obtained in accordance with the above processes may be isolated from the reaction mixtures and purified in known manner.

The starting material of formula II is new and may be produced by reacting pleuromutilin of formula IV with p-toluene sulfochloride.

The reaction is conveniently effected in an inert organic solvent such as toluene or benzene, preferably, however, in a solvent which simultaneously acts as acid-binding agent, such as pyridine. The reaction temperature should range between −15° and −10° C, the reaction period amounting to 2 to 4 hours.

The starting materials of formula IV may be obtained by reacting mutilin with a corresponding acid anhydride in the presence of catalytic amounts of sulphuric acid, at a temperature between room temperature and 80° C. In case the acid anhydride acts as solvent, it is not necessary to use an additional solvent. Otherwise it is necessary to effect the reaction in an inert organic solvent such as toluene or dimethyl formamide.

The starting materials of formulae IV and V are known and may be produced in accordance with the processes described in Austrian Patent Specification No. 250 770.

The starting materials obtained in accordance with the processes indicated above may be isolated from the reaction mixtures and purified in know manner.

The pleuromutilin derivatives of the invention are useful antibiotics and may be employed as animal feed supplements for increasing meat production. Owing to the small dose which needs to be employed in a ready-mixed feed and also non-excessive resorption of the derivatives by the animal, the consumption of meat from animals treated with the pleuromutilin derivatives does not involve danger of a resistance to antibiotic treatment developing in the consumer. Furthermore, the pleuromutilin derivatives of the invention are not employed in human therapy.

A suitable amount of pleuromutilin derivative of formula I in poultry feed ranges from between 2.5 and 90 mg of ready-mixed feed. A suitable amount for pig feed ranges between 10 and 180 mg per kg of ready-mixed feed. For calves and fattening cattle the pleuromutilin derivatives of formula I should be made available such that between about 25 and 120 mg of active agent are taken up daily by each animal.

Furthermore, the pleuromutilin derivatives of the invention are useful in veterinary medicine as indicated by their effect on pathogenic germs in animals. More particularly, the derivatives are active against staphylococci, and streptococci. In use, the derivatives may be provided in the form of a solution or paste and applied topically to the udder of a cow. The concentration of the derivatives in the solution or paste may conveniently be between 0.0001 and 5 mg/ml.

The derivatives are furthermore useful in treating illnesses in animals produced by PPLO, and the required amounts may be applied in the animal feed or drinking water. The feed should contain between 10 and 100 p.p.m of the pleuromutilin derivative in treating such illnesses.

In the following non-limitative Examples all temperatures are indicated in degrees Centigrade.

EXAMPLE 1

14-Desoxy-14-tosyloxyacetoxy-mutilin (compound of formula II)

95 g of pleuromutilin are dissolved in 350 cc of pyridine. The solution is cooled to −15° for 20 minutes, 65 g of p-toluene sulfochloride are added in one portion and the mixture is shaken until the material dissolves completely. The mixture is allowed to stand at −15° for 2 hours, and at ice water temperature for 1 hour, with frequent shaking. Working up is effected by pouring the mixture on 300 to 400 cc of ice water and extracting with 350 cc of chloroform. The cold organic solution is shaken out once with ice water, thrice with precooled 3 N sulphuric acid (a total of about 1 liter), once with water and once with a saturated sodium bicarbonate solution. The chloroform phase is separated, dried with sodium sulphate and concentrated by evaporation. Benzine (hexane fraction) is added to the residue which crystallizes after rubbing for a short period. After standing over night the crystals are filtered with suction, dried and recrystallized from about 350 cc of isopropanol, whereby 14-desoxy-14-tosyloxyacetoxy-mutilin, having a M.P. of 146°–148°, is obtained. After recrystallizing from acetone/hexane the M.P. rises to 147.5°–149.5°.

CH analysis: calculated: C 65.39 H 7.57%. found: C 65.02: H 7.70%.

EXAMPLE 2

14-Desoxy-14-monochloroacetoxy-mutilin [process (a)]

A suspension of 1 g of lithium chloride in 70 cc of acetone is added to a solution of 10.5 g of 14-desoxy-14- tosyloxyacetoxy-mutilin in 50 cc of acetone. The mixture is heated to 65° in an oil bath for 6 hours. After the reaction is complete, the precipitated solid material is removed by filtering with suction, the acetone solution is concentrated by evporation and the residue is taken up in chloroform. The chloroform phase is shaken out with water, dried with sodium sulphate and concentrated by evaporation. The oily residue is crystallized by rubbing with hexane. After recrystallizing from isopropanol. 14-desoxy-14-monochloroacetoxymutilin has a M.P. of 123°-124°.

CH analysis: calculated: C 66.55: H 8.38%. found: C 66.44: H 8.48%.

IR spectrum: δ C-Cl: 788 cm$^{-1}$

EXAMPLE 3

14-Desoxy-14-monoiodoacetoxy-mutilin [process (a)]

A solution of 17 g of sodium iodide in 200 cc of acetone is added to a solution of 52 g of 14-desoxy-14-tosyloxyacetoxymutilin in 150 cc. of acetone. The mixture is carefully heated in a water bath for 2 hours in order to complete the reaction. The resulting solid material is removed by filtering with suction and is washed with acetone. After concentrating the acetone filtrate by evaporation, an oily residue is obtained, which is taken up in chloroform and shaken out with water. The chloroform phase is concentrated by evaporation and the resulting oil is crystallized by rubbing with petroleum ether. After recrystallization from isopropanol the resulting 14-desoxy-14-monoiodoacetoxy-mutilin has a M.P. of 119°-120°.

EXAMPLE 4

14-Desoxy-14-monobromoacetoxy-mutilin [process (a)]

14-Desoxy-14-monobromoacetoxy-multilin, having a M.P. of 113°-118°, is obtained in a manner analogous to that described in Example 3 by reacting 53 g of 14-desoxy-14-toxyloxyacetoxy-mutilin with 12 g of sodium bromide in 400 cc of acetone and 80 cc of water for 7 hours.

EXAMPLE 5

14-Desoxy-14-thiccyanatoacetoxy-mutilin [process (a)]

5.3 g of 14-desoxy-14-tosyloxyacetoxy-mutilin are dissolved together with 1.1 g of potassium thiocyanate in 70 cc of methylethyl ketone, and the solution is heated to the boil. After a reaction period of ½ hour cooling is effected and the resulting potassium tosylate is filtered with suction. The methylethyl ketone solution is evaporated by dryness and the residue is further purified by dividing between chloroform and water. After drying the chloroform solution with sodium sulphate and concentrating by evaporation an oil is obtained, which crystallizes immediately upon rubbing with hexane. After recrystallizing from isopropanol the resulting 14-desoxy-14-thiocyanatoacetoxy-mutilin has a M.P. of 134°-136°.

CH analysis: calculated: C 65.83: H 7.93%. found: C 65.92: H 8.12%.

The infrared spectrum shows the thiocyanato band at 2155 cm$^{-1}$ (taken in Nujol).

EXAMPLE 6

14-Desoxy-14-azidoacetoxy-mutilin [process (a)]

A solution of 3.5 g of sodium azide in 32 cc of water is added to a solution of 26.6 g of 14-desoxy-14-tosyloxyacetoxymutilin in 250 cc of acetone and the solution is heated in a boiling water bath for 3 hours. The resulting solid material is filtered off and the filtrate is evaporated to dryness in a rotary vacuum evaporator. The residue is dissolved in 150 cc of chloroform and is shaken out twice with water. After dryng the chloroform phase with sodium sulphate, this is concentrated by evaporation and the oily residue is crystalized by the addition of hexane. After recrystallizing from isopropanol (twice) and acetone, 14-desoxy-14-azidoacetoxy-mutilin has a M.P. of 135°-140° (decomp.).

CH analysis: calculated: C 65.47: H 8.24%. found: C 65.45: H 8.27%.

EXAMPLE 7

(Dithiocarbonic acid O-ethyl-S-14-desoxypleuromutilyl ester [process (a)]

15.9 g of 14-desoxy-14-tosyloxyacetoxy-mutilin are dissolved in 50 cc of acetone and a solution of 4.8 g of potassium xanthate in 100 cc of acetone is added. It is recommended to combine the two solutions while warm (40°), since otherwise the immediately precipitating potassium tosylate is too fine. The precipitate is removed by centrifuging and the resulting acetone solution is concentrated by evaporation, whereby a yellow oil is obtained, which slowly crystallizes upon adding water. The crystalline product is drawn off by suction, is washed several times with water and dried. The resulting crystalline dithiocarbonic acid O-ethyl-S-14-desoxypleuromutilyl ester may subsequently be recrystallized from isopropanol.

CH analysis: calculated: C 62.20: H 7.94%. found: C 61.26: H 8.04%.

EXAMPLE 8

14-Desoxy-14-phenylmercaptoacetoxy-mutilin [process (a)]

0.46 g of sodium are dissolved in 50 cc of methanol. 2.2 cc of thiophenol are added to the solution, this is cooled with ice water and a solution of 10.6 g of 14-desoxy-14-tosyloxyacetoxy-mutilin in 30 cc of acetone is added portionwise. The mixture is first allowed to stand at room temperature while cooling with ice water and is subsequently heated on a boiling water bath for 15 minutes. The solvent is removed by evaporation on a rotary vacuum evaporator, the residue is taken up in 200 cc of chloroform and shaken out with water, whereupon the chloroform phase is separated, dried with sodium sulphate and concentrated by evaporation. The residue is crystallized by the addition of hexane, the precipitate is drawn off by suction and dried. The resulting 14-desoxy-14-phenylmercaptoacetoxy-mutilin has a M.P. of 120°-123°. The compound may be recrystallized from isopropanol.

CH analysis: calculated: C 71.46: H 8.14%. found C 71.26: H 8.25%.

EXAMPLE 9

14-Desoxy-14-acetoxy-mutilin [process (c)]

15 g of crude 14-desoxy-14-thiocyanatoacetoxy-mutilin are heated to the boil for 3 hours with 10 g of coarse aluminium amalgam powder in 30 cc of absolute ethanol. The mixture is then cooled and the thick pappy reaction product is concentrated by evaporation on a rotary vacuum evaporator. The residue is taken up in water/chloroform, is acidified with 200 cc of ice-cold hydrochloric acid (1:2), and after shaking out with water and drying with sodium sulphate, the chloroform phase is concentrated by evaporation. The oily residue crystallizes immediately upon adding benzine (hexane fraction). After recrystallizing from isopropanol (twice) and acetone 14-desoxy-14-acetoxy-mutilin has a M.P. of 185°-186° (previously sublimation).

CH analysis: calculated: C 72.89: H 9.46%. found: C 72.62: H 9.55%.

14-Desoxy-14-acetoxy-mutilin may likewise be obtained by reduction of 14-desoxy-14-bromoacetoxy-mutilin with coarse aluminium amalgam powder in the manner described above.

EXAMPLE 10

Mutilin-14-oxalic acid semiester [process (b)]

3.4 g of pleuromutilin, 30 g of activated manganese dioxide and 2 g of anhydrous potassium carbonate are heated to the boil at reflux for 4 to 5 hours in 50 cc of pure acetone. The mixture is subsequently filtered with suction and washing is effected with acetone. The acetone solutions are discarded. The reaction product is obtained by heating the residue to the boil with 250 to 300 cc of absolute ethanol. The mixture is then filtered with suction, the turbid filtrate is clarified with Filter-Cel and the alcoholic solution is evaporated to dryness. The residue is distilled off twice with benzene. After taking up in acetone and scratching a jelly-like precipitate of the potassium salt of mutilin-14-oxalic acid semiester is obtained. This is dissolved in water and the aqueous solution is acidified with dilute hydrochloric acid, whereby mutilin-14-oxalic acid semiester is obtained.

Analysis: calculated: C 67.32: H 8.22%. found: C 66.80: H 8.27%.

EXAMPLE 1

14-Desoxy-14-aminoacetoxy-dihydro-mutilin [process (d)]

4.0 g of 14-desoxy-14-azidoacetoxy-mutilin are hydrogenated in 50 cc of glacial acetic acid, in the presence of 1.5 g of palladium charcoal (10%) at room temperature for 3 hours. After concentrating the glacial acetic acid solution, this is taken up in water, is filtered to remove the undissolved material and is made alkaline by the addition of sodium bicarbonate. 14-Desoxy-14-aminoacetoxy-dihydro-mutilin precipitates and has a M.P. of 178°-182° (decomp.) after recrystallization from a small amount of isopropanol. Acetate: M.P. 166°-172°.

EXAMPLE 12

14-Desoxy-14-diazoacetoxy-dihydro-mutilin [process (e)]

0.3 g of 14-desoxy-14-aminoacetoxy-dihydro-mutilin are dissolved in 40 cc of water and 8 cc of 10 H hydrochloric acid, and 0.1 g of sodium nitrite is added while cooling. 14-Desoxy-14-diazoacetoxy-dihydro-mutilin is obtained and is filtered off. IR spectrum: absorption at 2100 cm$^{-1}$.

EXAMPLE 13

11-Desoxy-11-acetoxy-mutilin [process (f)]

a. Pleuromutilin diacetate.

10 g of pleuromutilin are suspended in 60 cc of acetic anhydride and 2 drops of concentrated sulphuric acid are added while shaking. After the heat of the reaction subsides, the mixture is allowed to stand over night and the excess acetic anhydride is removed in a water pump vacuum at 50°. The residue crystallizes upon adding 50 cc of water and 2 g of sodium hydrogen carbonate, and after filtering with suction and drying is recrystallized from hexane. M.P. 142°-145°.

b. 11-Desoxy-11-acetoxy-mutilin.

5 g of pleuromutilin diacetate are heated to the boil for 35 minutes in 60 cc of acetone/6 N hydrochloric acid (2:1). The solvent is removed by evaporation and the resulting 11-desoxy-11-acetoxy-mutilin has a M.P. of 161°-163°.

EXAMPLE 14

14-Desoxy-14-acetoxy-mutilin [process (g)]

a. Mutilin-11,14-diacetate.

60 cc of acetic anhydride are added to 10 g of mutilin and 2 drops of concentrated sulphuric acid are added to the mixture while shaking well. The solution heats itself strongly and is allowed to stand over night at room temperature. The main portion of the diacetate which precipitates from the reaction mixture is crystalline form, is drawn off by suction, is washed with a small amount of alcohol and dried. A further amount of diacetate may be isolated from the mother liquor. M.P. 206°-208°.

b. 14-Desoxy-14-acetoxy-mutilin.

4.0 g of mutilin-11,14-diacetate are dissolved in 50 cc of ethanol, a solution of 0.6 g of sodium hydroxide in 10 cc of water is added, and the mixture is heated on a boiling water bath for 90 minutes. The clear yellow solution is concentrated by evaporation and the residue is taken up in ethyl acetate, washed and dried. The solvent is evaporated and the residue is treated ether and filtered with suction. After recrystallization from a small amount of acetone, 14-desoxy-14-acetoxy-mutilin has a M.P. of 183-185° and all its properties are identical with those of the product obtained in Example 9.

EXAMPLE 15

14-Desoxy-14-methylmercaptoacetoxy-mutilin [process (a)]

10.6 g of 14-desoxy-14-tosyloxyacetoxy-mutilin are dissolved in 20 cc of acetone. A solution of 0.5 g of sodium in 20 cc of absolute alcohol, additionally containing 1.2 cc of cooled methylmercaptan, is added in an atmosphere of nitrogen. The reaction mixture is filtered, the filtrate is heated to 50° for 20 minutes and is concentrated on a rotary vacuum evaporator. The residue is divided between water and ethyl acetate and the ethyl acetate phase is concentrated by evaporation. The resulting crude product is oily and cannot be obtained in crystalline form even after chromatography. The purified product shows a rapidly migrating spott in the thin layer chromatogram.

EXAMPLE 16

14-Desoxy-14-p-hydroxyphenylmercaptoacetoxy-mutilin [process (a)]

0.5 g of sodium in 15 cc of absolute ethanol are added at room temperature to 10.6 g of 14-desoxy-14-tosyloxyacetoxy-mutilin, 3.15 g of thiohydroquinone and 30 cc of acetone in a purified atmosphere of nitrogen, and the mixture is shaken. The reaction mixture is filtered. After 10 minutes the mixture is heated to 50°-60° on a water bath for 20 minutes and is acidified with acetic acid. After concentrating by evaporation, water is added to the mixture and the reaction product is extracted with ethyl acetate. After evaporating the solvent, an oil is obtained which slowly crystallizes after the addition of water; the crystalline product is dried in an exsiccator and is recrystallized from chloroform/hexane. A thin layer chromatographically homogeneous material is obtained. The M.P. is not sharp.

IR spectrum: carbonyl bands at 1735 and 1700 cm$^{-1}$, aromatic substance bands at 1602, 1582 and 837 cm$^{-1}$.

EXAMPLE 17

14-Desoxy-14-(2'-carboxyphenylmercaptoacetoxy)-mutilin [process (a)]

5.3 g of 14-desoxy-14-tosyloxyacetoxy-mutilin are dissolved in 20 cc of acetone and 1.5 g of thiosalicylic acid are added. After mixing well and passing a stream of nitrogen through the solution, a solution of 0.46 g of sodium in 40 cc of absolute ethanol is added, the reaction mixture is shaken and subsequently kept at 50°-60° for 20 minutes. The resulting precipitate is removed. The reaction mixture is subsequently concentrated by evaporation, the residue is taken up in water and the aqueous phase is successively extracted with toluene, ethyl acetate and hexane. After acidifying with dilute hydrochloric acid, a precipitate results, which is again dissolved with sodium bicarbonate in 200 cc of water. The bicarbonate solution is filtered and acidified, whereby crystalline 14-desoxy-14-(2'-carboxyphenyl-mercaptoacetoxy)-mutilin is obtained.

Equivalent weight: calculated 514. found 492.

EXAMPLE 18

14-Desoxy-14-(2',5'-dihydroxyphenylmercaptoacetoxy)-mutilin [process (a)]

5.3 g of 14-desoxy-14-tosyloxyacetoxy-mutilin and 1.42 g of 2-mercaptohydroquinone are dissolved in 20 cc of dry acetone and a freshly prepared solution of 0.46 g of sodium in 20 cc of absolute ethanol is added in the absence of oxygen. After allowing the reaction mixture to stand for several hours (6 hours) at approx. 20°, the reaction is complete. The reaction mixture is then acidified with a few drops of 50% acetic acid. Working up is effected by concentrating the reaction mixture by evaporation and treating the residue with water. The resulting oil is purified by column chromatography on silica gel.

IR spectrum: carbonyl band at 1715 cm$^{-1}$.

The broad band shows inflections at 1680, 1725 and 1740 cm$^{-1}$, bands at 1635 (broad), aromatic substance bands at 870, 820 and 785 cm.

EXAMPLE 19

14-Desoxy-14-(2',4'-dihydroxyphenylmercaptoacetoxy)-mutilin [process (a)]

14-Desoxy-14-(2',4'-dihydroxphenylmercaptoacctoxy)-mutilin is obtained in accordance with the process described in Example 18, by reacting 5.3 g of 14-desoxy-14-tosyloxyacetoxy-mutilin with 1.42 g of 2,4-dihydroxy-thiophenol in 20 cc of dry acetone, in the presence of 0.46 g of sodium in 20 cc of absolute ethanol. The compound is purified by dissolving in chloroform (or ethyl acetate) and is again crystallized by the addition of hexane.

Thin layer chromatography on silica gel C plates:
Eluant: water-saturated diethyl ether
R$_f$ values:
  dihydroxy compound: 0.35
  pleuromutilin: 0.40
  mutilin: 0.58

The M.P. is not sharp due to decomposition. A further purification may be effected by column chromatography on silica gel.

EXAMPLE 20

14-Desoxy-14-(2',3'-dihydroxypropylmercaptoacetoxy)-mutilin [process (a)]

5.3 g of 14-desoxy-14-tosyloxyacetoxy-mutilin are reacted with 1 cc of thioglycerin in 15 cc of acetone in the presence of 0.24 g of sodium in 20 cc of absolute ethanol. The commencement of the reaction is accompanied by a precipitation of sodium tosylate. Working up is effected by filtration, concentration of the reaction mixture by evaporation and treatment of the residue with water. An oil separates, which cannot be made to crystallize.

EXAMPLE 21

14-Desoxy-14-(2'-hydroxyethylmercaptoacetoxy)-mutilin [process (a)]

5.3 g of 14-desoxy-14-tosyloxyacetoxy-mutilin are reacted with 0.78 g of 2-mercapto-ethanol in 15 cc of acetone, in the presence of 0.24 g of sodium in 20 cc of absolute ethanol. The commencement of the reaction is accompanied by a precipitation of sodium tosylate. Working up is effected by filtration, concentration of the reaction mixture by evaporation and treatment of the residue with water. An oil separates, which cannot be made to crystallize.

EXAMPLE 22

14-Desoxy-14-(carboxymethylmercaptoacetoxy)-mutilin [process (a)]

0.5 g of sodium in 20 cc of absolute ethanol are added to 5.3 g of 14-desoxy-14-tosyloxyacetoxy-mutilin, 0.9 cc of freshly distilled thioglycolic acid and 15 cc of acetone, and the mixture is stirred at room temperature for 15 minutes, and at 50° for 15 minutes. The resulting precipitate is removed. After evaporating the solvent the residue is taken up in water, extracted once with toluene, and the aqueous phase is acidified with dilute acetic acid. A jelly-like precipitate is obtained, which does not crystallize. It is taken up in ethyl acetate, and after drying and evaporating the solvent, yields a viscous oil.

EXAMPLE 23

14-Desoxy-14-[(N,N-tetramethylene-thiocarbamoyl)-mercaptoacetoxy]-mutilin [process (a)]

5.3 g of 14-desoxy-14-tosyloxyacetoxy-mutilin and 1.7 g of sodium-N,N-tetramethylene dithiocarbamate are dissolved in 20 cc of dimethyl formamide, whereby a distinct heat effect developed. The reaction mixture is kept at 50° for ½ hour and is then poured on ice water, whereby the reaction product precipitates. After a short period it can be filtered with suction and washed with water.

What is claimed is:
1. 14-desoxy-14-thiocyanatoacetoxy-mutilin.

* * * * *